(12) United States Patent
Leung et al.

(10) Patent No.: US 11,826,075 B2
(45) Date of Patent: Nov. 28, 2023

(54) ELONGATED MEDICAL ASSEMBLY

(71) Applicant: Boston Scientific Medical Device Limited, Ballybrit (IE)

(72) Inventors: Jackie Leung, Richmond Hill (CA); Eduardo Moriyama, Richmond (CA); Gareth Davies, Toronto (CA); Kaylie Lau, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 282 days.

(21) Appl. No.: 17/223,122

(22) Filed: Apr. 6, 2021

(65) Prior Publication Data

US 2021/0307783 A1 Oct. 7, 2021

Related U.S. Application Data

(60) Provisional application No. 63/006,427, filed on Apr. 7, 2020.

(51) Int. Cl.
*A61B 17/34* (2006.01)
*A61B 17/00* (2006.01)

(52) U.S. Cl.
CPC .... *A61B 17/3478* (2013.01); *A61B 17/00234* (2013.01); *A61B 2017/00247* (2013.01); *A61B 2017/00336* (2013.01); *A61B 2017/3488* (2013.01)

(58) Field of Classification Search
CPC ........ A61B 17/00234; A61B 17/22072; A61B 17/22077; A61B 17/3405; A61B 17/3445; A61B 17/3468; A61B 17/3478; A61B 2017/00247; A61B 2017/00336; A61B 2017/3403; A61B 2017/3488; A61B 17/3403; A61B 2017/22072; A61B 2017/22077; A61B 2017/3405; A61B 2017/3445

See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |

(Continued)

*Primary Examiner* — Ryan J. Severson
(74) *Attorney, Agent, or Firm* — Nelson Mullins Riley & Scarborough (57) ABSTRACT

An elongated medical assembly is configured to be maneuverable proximate to a first biological feature of a patient. The elongated medical assembly is also configured to facilitate movement along an elongated length of the elongated medical assembly of a first medical device and a second medical device.

3 Claims, 4 Drawing Sheets

(56) References Cited

U.S. PATENT DOCUMENTS

| | | | |
|---|---|---|---|
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,425,705 A * | 6/1995 | Evard ............... A61B 17/06061 604/36 |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Igler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,475,226 B1 * | 11/2002 | Belef ................... A61B 17/11 606/170 |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |

(56) References Cited

U.S. PATENT DOCUMENTS

| | | | |
|---|---|---|---|
| 6,702,811 B2 | 3/2004 | Stewart et al. | |
| 6,709,444 B1 | 3/2004 | Makower | |
| 6,723,052 B2 | 4/2004 | Mills | |
| 6,733,511 B2 | 5/2004 | Hall et al. | |
| 6,740,103 B2 | 5/2004 | Hall et al. | |
| 6,752,800 B1 | 6/2004 | Winston et al. | |
| 6,755,816 B2 | 6/2004 | Ritter et al. | |
| 6,811,544 B2 | 11/2004 | Schaer | |
| 6,814,733 B2 | 11/2004 | Schwartz et al. | |
| 6,820,614 B2 | 11/2004 | Bonutti | |
| 6,834,201 B2 | 12/2004 | Gillies et al. | |
| 6,842,639 B1 | 1/2005 | Winston et al. | |
| 6,852,109 B2 | 2/2005 | Winston et al. | |
| 6,855,143 B2 | 2/2005 | Davison et al. | |
| 6,860,856 B2 | 3/2005 | Ward et al. | |
| 6,869,431 B2 | 3/2005 | Maguire et al. | |
| 6,911,026 B1 | 6/2005 | Hall et al. | |
| 6,951,554 B2 | 10/2005 | Johansen et al. | |
| 6,951,555 B1 | 10/2005 | Suresh et al. | |
| 6,955,675 B2 | 10/2005 | Jain | |
| 6,970,732 B2 | 11/2005 | Winston et al. | |
| 6,980,843 B2 | 12/2005 | Eng et al. | |
| 7,029,470 B2 | 4/2006 | Francischelli et al. | |
| 7,056,294 B2 | 6/2006 | Khairkhahan et al. | |
| 7,083,566 B2 | 8/2006 | Tornes et al. | |
| 7,112,197 B2 | 9/2006 | Hartley et al. | |
| 7,335,197 B2 | 2/2008 | Sage et al. | |
| 7,618,430 B2 | 11/2009 | Scheib | |
| 7,651,492 B2 | 1/2010 | Wham | |
| 7,666,203 B2 | 2/2010 | Chanduszko et al. | |
| 7,678,081 B2 | 3/2010 | Whiting et al. | |
| 7,682,360 B2 | 3/2010 | Guerra | |
| 7,828,796 B2 | 11/2010 | Wong et al. | |
| 7,900,928 B2 | 3/2011 | Held et al. | |
| 8,192,425 B2 | 6/2012 | Mirza et al. | |
| 8,257,323 B2 | 9/2012 | Joseph et al. | |
| 8,388,549 B2 | 3/2013 | Paul et al. | |
| 8,500,697 B2 | 8/2013 | Kurth et al. | |
| 8,709,007 B2* | 4/2014 | Vaska | A61B 18/00 606/41 |
| 9,242,122 B2* | 1/2016 | Tsoref | A61N 7/02 |
| 9,561,345 B2* | 2/2017 | Garrison | A61M 25/0023 |
| 10,071,226 B2* | 9/2018 | Hsueh | A61M 25/09 |
| 11,339,579 B1 | 5/2022 | Stearns | |
| 2001/0012934 A1 | 8/2001 | Chandrasekaran et al. | |
| 2001/0021867 A1 | 9/2001 | Kordis et al. | |
| 2002/0019644 A1 | 2/2002 | Hastings et al. | |
| 2002/0022781 A1 | 2/2002 | McIntire et al. | |
| 2002/0022836 A1 | 2/2002 | Goble et al. | |
| 2002/0035361 A1 | 3/2002 | Houser et al. | |
| 2002/0087153 A1 | 7/2002 | Roschak et al. | |
| 2002/0087156 A1 | 7/2002 | Maguire et al. | |
| 2002/0111618 A1 | 8/2002 | Stewart et al. | |
| 2002/0123749 A1 | 9/2002 | Jain | |
| 2002/0147485 A1 | 10/2002 | Mamo et al. | |
| 2002/0169377 A1 | 11/2002 | Khairkhahan et al. | |
| 2002/0188302 A1 | 12/2002 | Berg et al. | |
| 2002/0198521 A1 | 12/2002 | Maguire | |
| 2003/0032929 A1 | 2/2003 | McGuckin | |
| 2003/0040742 A1 | 2/2003 | Underwood et al. | |
| 2003/0144658 A1 | 7/2003 | Schwartz et al. | |
| 2003/0158480 A1 | 8/2003 | Tornes et al. | |
| 2003/0163153 A1 | 8/2003 | Scheib | |
| 2003/0225392 A1 | 12/2003 | McMichael et al. | |
| 2004/0015162 A1 | 1/2004 | McGaffigan | |
| 2004/0024396 A1 | 2/2004 | Eggers | |
| 2004/0030328 A1 | 2/2004 | Eggers et al. | |
| 2004/0044350 A1 | 3/2004 | Martin et al. | |
| 2004/0073243 A1 | 4/2004 | Sepetka et al. | |
| 2004/0077948 A1 | 4/2004 | Violante et al. | |
| 2004/0116851 A1 | 6/2004 | Johansen et al. | |
| 2004/0127963 A1 | 7/2004 | Uchida et al. | |
| 2004/0133113 A1 | 7/2004 | Krishnan | |
| 2004/0133130 A1 | 7/2004 | Ferry et al. | |
| 2004/0143256 A1 | 7/2004 | Bednarek | |
| 2004/0147950 A1 | 7/2004 | Mueller et al. | |
| 2004/0153098 A1* | 8/2004 | Chin | A61B 17/3421 600/374 |
| 2004/0162568 A1* | 8/2004 | Saadat | A61B 1/2736 606/139 |
| 2004/0181213 A1 | 9/2004 | Gondo | |
| 2004/0230188 A1 | 11/2004 | Cioanta et al. | |
| 2004/0254597 A1* | 12/2004 | Schwartz | A61B 17/3207 606/167 |
| 2005/0004585 A1 | 1/2005 | Hall et al. | |
| 2005/0010208 A1 | 1/2005 | Winston et al. | |
| 2005/0049628 A1 | 3/2005 | Schweikert et al. | |
| 2005/0059966 A1 | 3/2005 | McClurken et al. | |
| 2005/0065507 A1 | 3/2005 | Hartley et al. | |
| 2005/0085806 A1 | 4/2005 | Auge et al. | |
| 2005/0096529 A1 | 5/2005 | Cooper et al. | |
| 2005/0101984 A1 | 5/2005 | Chanduszko et al. | |
| 2005/0119556 A1 | 6/2005 | Gillies et al. | |
| 2005/0137527 A1 | 6/2005 | Kunin | |
| 2005/0149012 A1 | 7/2005 | Penny et al. | |
| 2005/0165466 A1* | 7/2005 | Morris | A61B 17/00234 607/116 |
| 2005/0203504 A1 | 9/2005 | Wham et al. | |
| 2005/0203507 A1 | 9/2005 | Truckai et al. | |
| 2005/0261607 A1 | 11/2005 | Johansen et al. | |
| 2005/0288631 A1 | 12/2005 | Lewis et al. | |
| 2006/0041253 A1 | 2/2006 | Newton et al. | |
| 2006/0074398 A1 | 4/2006 | Whiting et al. | |
| 2006/0079769 A1 | 4/2006 | Whiting et al. | |
| 2006/0079787 A1 | 4/2006 | Whiting et al. | |
| 2006/0079884 A1 | 4/2006 | Manzo et al. | |
| 2006/0085054 A1 | 4/2006 | Zikorus et al. | |
| 2006/0089638 A1 | 4/2006 | Carmel et al. | |
| 2006/0106375 A1 | 5/2006 | Werneth et al. | |
| 2006/0135962 A1 | 6/2006 | Kick et al. | |
| 2006/0142756 A1 | 6/2006 | Davies et al. | |
| 2006/0161185 A1* | 7/2006 | Saadat | A61B 17/0487 606/153 |
| 2006/0189972 A1 | 8/2006 | Grossman | |
| 2006/0241586 A1 | 10/2006 | Wilk | |
| 2006/0247672 A1 | 11/2006 | Vidlund et al. | |
| 2006/0253183 A1* | 11/2006 | Thagalingam | A61N 1/0502 607/126 |
| 2006/0264927 A1 | 11/2006 | Ryan | |
| 2006/0276710 A1 | 12/2006 | Krishnan | |
| 2007/0060879 A1 | 3/2007 | Weitzner et al. | |
| 2007/0066975 A1 | 3/2007 | Wong et al. | |
| 2007/0118099 A1 | 5/2007 | Trout | |
| 2007/0123964 A1 | 5/2007 | Davies et al. | |
| 2007/0167775 A1 | 7/2007 | Kochavi et al. | |
| 2007/0208256 A1 | 9/2007 | Marilla | |
| 2007/0225681 A1 | 9/2007 | House | |
| 2007/0270791 A1 | 11/2007 | Wang et al. | |
| 2008/0039865 A1 | 2/2008 | Shaher et al. | |
| 2008/0042360 A1 | 2/2008 | Veikley | |
| 2008/0082136 A1* | 4/2008 | Gaudiani | A61B 6/481 607/9 |
| 2008/0086120 A1 | 4/2008 | Mirza et al. | |
| 2008/0097213 A1 | 4/2008 | Carlson et al. | |
| 2008/0108987 A1 | 5/2008 | Bruszewski et al. | |
| 2008/0146918 A1 | 6/2008 | Magnin et al. | |
| 2008/0171934 A1 | 7/2008 | Greenan et al. | |
| 2008/0208121 A1 | 8/2008 | Youssef et al. | |
| 2008/0275439 A1 | 11/2008 | Francischelli et al. | |
| 2008/0294174 A1* | 11/2008 | Bardsley | A61B 17/3415 606/186 |
| 2009/0105742 A1 | 4/2009 | Kurth et al. | |
| 2009/0138009 A1 | 5/2009 | Viswanathan et al. | |
| 2009/0163850 A1 | 6/2009 | Betts et al. | |
| 2009/0177114 A1 | 7/2009 | Chin et al. | |
| 2009/0264977 A1 | 10/2009 | Bruszewski et al. | |
| 2010/0087789 A1 | 4/2010 | Leeflang et al. | |
| 2010/0125282 A1 | 5/2010 | Machek et al. | |
| 2010/0168684 A1 | 7/2010 | Ryan | |
| 2010/0179632 A1 | 7/2010 | Bruszewski et al. | |
| 2010/0191142 A1 | 7/2010 | Paul et al. | |
| 2010/0194047 A1 | 8/2010 | Sauerwine | |
| 2011/0046619 A1 | 2/2011 | Ducharme | |

(56) References Cited

U.S. PATENT DOCUMENTS

| | | |
|---|---|---|
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0148828 A1* | 5/2014 | Ewers ............... A61B 17/062 606/153 |
| 2014/0206987 A1 | 7/2014 | Urbanski et al. |
| 2014/0277054 A1* | 9/2014 | McNamara ........ A61B 17/3403 606/185 |
| 2014/0296769 A1 | 10/2014 | Hyde et al. |
| 2015/0112188 A1* | 4/2015 | Stigall ............... A61B 17/064 600/424 |
| 2015/0359556 A1* | 12/2015 | Vardi ............ A61B 17/320016 606/170 |
| 2016/0220741 A1 | 8/2016 | Garrison et al. |
| 2017/0007310 A1* | 1/2017 | Rajagopalan .... A61B 17/00234 |
| 2017/0245885 A1* | 8/2017 | Lenker ............... A61B 17/3478 |
| 2018/0103985 A1* | 4/2018 | Maini ................ A61B 17/3403 |
| 2019/0021763 A1 | 1/2019 | Zhou et al. |
| 2019/0029750 A1* | 1/2019 | Maini ................ A61M 25/0662 |
| 2019/0247035 A1 | 8/2019 | Gittard et al. |
| 2019/0336163 A1* | 11/2019 | McNamara ........ A61B 17/3403 |
| 2021/0307783 A1* | 10/2021 | Leung ............... A61B 17/3478 |
| 2021/0330355 A1* | 10/2021 | Leung ............... A61B 17/3478 |

\* cited by examiner

ELONGATED MEDICAL ASSEMBLY

TECHNICAL FIELD

This document relates to the technical field of (and is not limited to) an elongated medical assembly configured to facilitate movement of a first medical device and a second medical device; this document also relates to the technical field of (and is not limited to) an elongated medical assembly for a puncture device and an anchor device; and/or this document also relates to the technical field of (and is not limited to) a synergistic combination of an elongated medical assembly, a puncture device, and an anchor device (and methods therefor).

BACKGROUND

Known medical devices are configured to facilitate a medical procedure, and help healthcare providers diagnose and/or treat medical conditions of patients.

SUMMARY

It will be appreciated that there exists a need to mitigate (at least in part) at least one problem associated with the existing (known) medical devices. After much study of, and experimentation with, the existing (known) medical devices, an understanding (at least in part) of the problem and its solution have been identified (at least in part) and are articulated (at least in part) as follows:

Laceration of the valve leaflets may be a preventative procedure performed to minimize the risk of obstruction of the right coronary artery (RCA) of the heart of a patient (which may be performed after transcatheter aortic valve replacement (TAVR)). This procedure first includes the puncture and traversal of the leaflet (of the heart), for which the puncture (the hole) may be formed by a medical wire, etc. The puncture location may be a critical factor in the outcome of the procedure.

For instance, for the BASILICA and LAMPOON procedures for lacerating the valve leaflet (of the heart), the operator (user or surgeon) may rely on medical imaging (medical imaging obtained during the procedure) to identify the correct valve leaflet and followed by positioning (maneuvering) the puncturing device (the puncture wire) onto (against) the valve leaflet that is identified in the medical image.

What may be needed or desired is an anchor point configured to aid in guiding the puncture device to the desired position within the patient.

It may be desirable to provide a medical anchor device, such as an anchor wire, that may improve positioning of the puncture device wire. The medical anchor device may be maneuvered (by the operator or user), at least in part, into an opening of the right coronary artery of the heart of the patient), and anchored thereto.

The medical anchor device may be configured to provide or to serve as a reference for the operator to help target the correct or optimal location of the leaflet for subsequent puncturing of the leaflet of the patient.

What may be desired is an apparatus configured to facilitate laceration (puncturing) of valve leaflets in the heart of the patient.

The medical anchor device may be advanced and retracted in (along) a medical sheath, and may form a bend (such as a perpendicular bend) when advanced from (extended away from, or advanced therefrom) the interior of the medical sheath. The puncture device may share the elongated medical assembly and may also be advanced and retracted by the operator, etc.

The medical anchor device is configured to be retractable into a medical sheath assembly. The medical anchor device (also called a wire) is configured to form a bend (such as a perpendicular bend, and any equivalent thereof) when (once or after) the medical anchor device is extended out from (maneuvered from) the interior of the medical sheath assembly (this is done in such a way that the medical anchor device enters (extends into) the right coronary artery). For instance, this arrangement may be achieved (preferably) by having the medical anchor device include a shape memory material and/or any equivalent thereof (such as, a steering mechanism, etc.). In accordance with a preferred embodiment, the medical anchor device may be stiff enough to hold (position) the medical sheath assembly in place (in a stationary position) when or after the medical anchor device is inserted into the right coronary artery (RCA), etc. Other embodiments, for instance, may include arranging for selective stable positioning of (relatively stationary deployment of) the medical anchor device by utilization of a selectively expandable and collapsible system. The selectively expandable and collapsible system may include, for instance, a flexible cage structure, a flexible coil structure, a balloon structure (expandable and collapsible balloon), etc., and any equivalent thereof. The selectively expandable and collapsible system is configured to assist or facilitate selective anchoring of the medical sheath assembly to a relatively stable position located within the patient. For instance, the stable position may be located inside the RCA, etc. Generally, the medical anchor device (anchor device) may be configured to be selectively expandable and collapsible in such a way that the medical anchor device selectively anchors the medical sheath to (or proximate to) a biological feature of (located in) the patient.

The puncture device (also called a puncture wire) may include an insulated wire with an electrode positioned at the distal section, and is configured to perforate (puncture) soft tissue with radio frequency energy, and any equivalent thereof. The puncture device may share the same medical sheath assembly as the medical anchor device so that their proximal portions may be oriented in the same direction. For instance, energy may be delivered to the puncture device via a generator device electrically connected at the proximal end of the puncture device, etc.

The medical sheath assembly may be configured to facilitate movement of the puncture device and the anchor device as a single medical device. The medical sheath assembly may be configured to allow the puncture device and the anchor device to be advanced and/or retracted. The anchor device may include a shape and material that may be variable and/or steerable. The puncture device may include a mechanical puncture device. The puncture device may include features to simplify the BASILICA workflow or the LAMPOON workflow after the puncture is formed, such as having a proximal electrode for laceration and pre-kinking of the wire at the proximal electrode.

To mitigate, at least in part, at least one problem associated with the existing technology, there is provided (in accordance with a major aspect) an apparatus. The apparatus includes and is not limited to an elongated medical assembly configured to be maneuverable proximate to a first biological feature of a patient. The elongated medical assembly is also configured to facilitate movement of a first medical device and a second medical device along an elongated length of the elongated medical assembly. More specifically, the elongated medical assembly is configured to be maneuverable proximate to a first biological feature of a patient, and the elongated medical assembly has an elongated length, and the elongated medical assembly is also configured to facilitate movement of a first medical device and a second medical device along the elongated length of the elongated medical assembly.

To mitigate, at least in part, at least one problem associated with the existing technology, there is provided (in accordance with a major aspect) an apparatus. The apparatus includes and is not limited to an apparatus including (and is not limited to) a synergistic combination of (A) an elongated medical assembly configured to be maneuverable proximate to a first biological feature of a patient, (B) a first medical device configured to be movable along the elongated medical assembly for facilitated movement along an elongated length of the elongated medical assembly, and (C) a second medical device configured to be movable along the elongated medical assembly for facilitated movement along an elongated length of the elongated medical assembly.

To mitigate, at least in part, at least one problem associated with the existing technology, there is provided (in accordance with a major aspect) an apparatus. The apparatus includes and is not limited to an elongated medical assembly configured to be maneuverable proximate to a first biological feature of a patient. A puncture device is configured to be, at least in part, supported for maneuvered movement along the elongated medical assembly. An anchor device is configured to be, at least in part, supported for maneuvered movement along the elongated medical assembly.

To mitigate, at least in part, at least one problem associated with the existing technology, there is provided (in accordance with a major aspect) an apparatus. The apparatus includes an elongated medical assembly configured to be maneuverable proximate to a first biological feature of a patient; the elongated medical assembly has a distal port assembly leading to a lumen assembly defined along, at least in part, an elongated length of the elongated medical assembly. A puncture device is configured to be, at least in part, receivable into (extendable from and retractable into) the distal port assembly of the elongated medical assembly, and extendable, at least in part, along the lumen assembly of the elongated medical assembly (after the puncture device, in use, is received, at least in part, into the distal port assembly of the elongated medical assembly). An anchor device is configured to be, at least in part, receivable into (extendable from and retractable into) the distal port assembly of the elongated medical assembly, and extendable, at least in part, along the lumen assembly of the elongated medical assembly (after the puncture device, in use, is received, at least in part, into the anchor device of the elongated medical assembly).

To mitigate, at least in part, at least one problem associated with the existing technology, there is provided (in accordance with a major aspect) a method. The method is for operating an elongated medical assembly. The method includes and is not limited to maneuvering, at least in part, the elongated medical assembly to a position located proximate to a first biological feature of a patient. The method also includes maneuvering, at least in part, a puncture device along the elongated medical assembly. The method also includes maneuvering, at least in part, an anchor device along the elongated medical assembly.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS elongated medical assembly 102
medical sheath assembly 103
distal port assembly 104 (also called distal assembly)
lumen assembly 106
second medical device 108
puncture device 109
first medical device 110
anchor device 111
interior elongated wall 112
second movement direction 208
first distal port 301
second distal port 302
first lumen 401
second lumen 402
first movement direction 210
patient 900
first biological feature 901
second biological feature 902
puncture hole 908
biological structure 910

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

FIG. 1, FIG. 2, FIG. 3 and FIG. 4 depict side views of embodiments of an elongated medical assembly 102.

Figure 1:
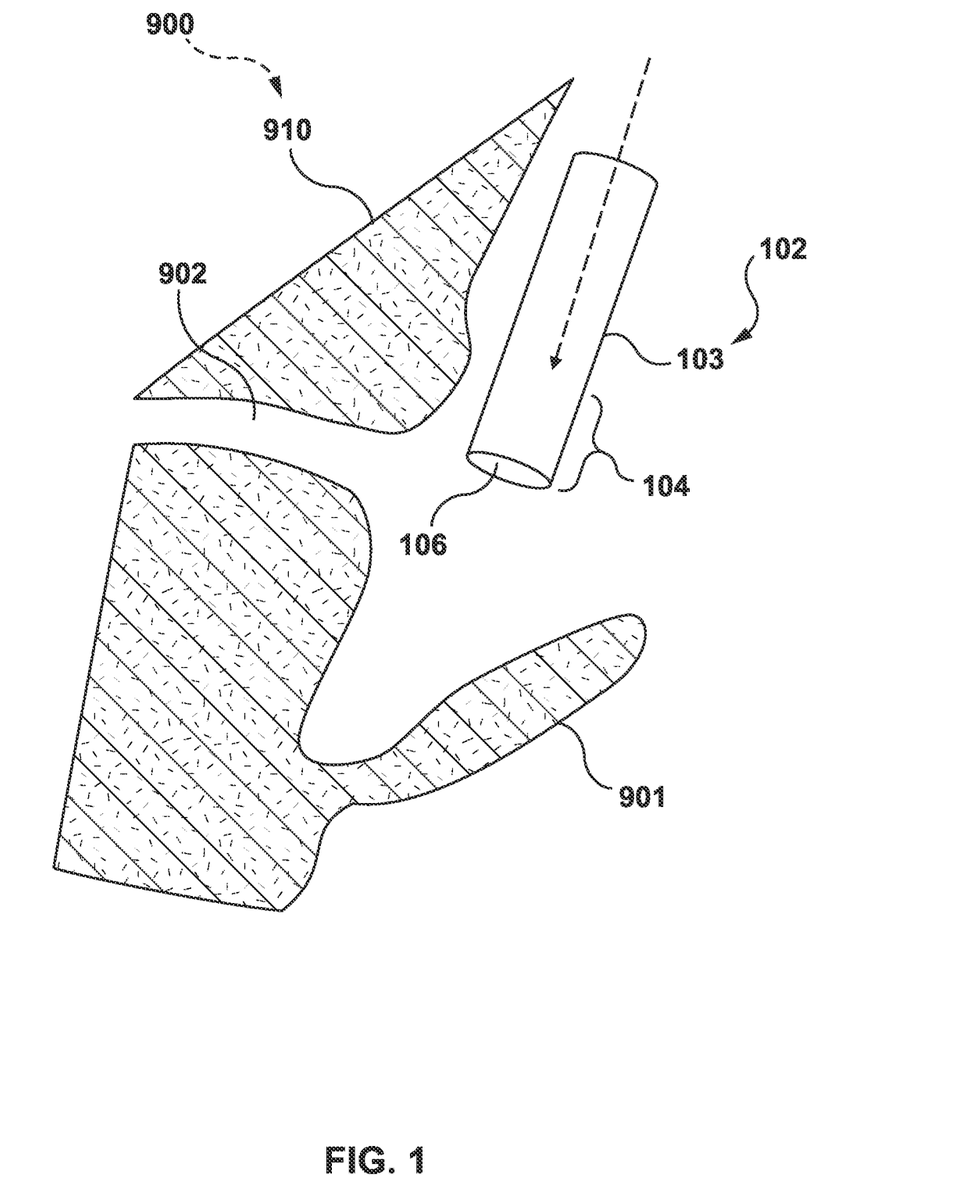
FIG. 1, FIG. 2, FIG. 3 and FIG. 4 depict side views of embodiments of an elongated medical assembly (such as, a medical sheath assembly).

Referring to the embodiment as depicted in FIG. 1, the elongated medical assembly 102 is configured to be inserted into (at least in part) a patient 900. More specifically, the elongated medical assembly 102 is configured to be inserted into a confined or tortuous space defined by the patient 900. The elongated medical assembly 102 includes, preferably, a flexible tube (made from a medical grade material, and any equivalent thereof). The material of the elongated medical assembly 102 is (preferably) impermeable by, and compatible with, any bodily fluid located in the patient 900. Once inserted into the patient 900, the elongated medical assembly 102 is configured to be maneuvered (to be movable by a surgeon performing a procedure) toward a position located proximate to a biological structure 910 (such as, the heart, etc.) of the patient 900. It will be appreciated that the term "proximate to" may include a position located within (at least in part) the biological structure 910, a position located (at least in part) outside of the biological structure 910, etc. The elongated medical assembly 102 is (preferably) configured to guide the insertion of (and movement of) at least one, or more, medical devices along the elongated length of the elongated medical assembly 102 (also called a flexible medical guidewire assembly) and each medical device includes (in accordance with a preferred embodiment) biocompatible materials and/or properties configured to have suitable or sufficient device attributes (such as, dielectric strength, thermal performance, insulation and corrosion, water and heat resistance) for safe performance, and to comply with industrial and regulatory safety standards (or compatible for medical usage). Reference is made to the following publication for consideration in the selection of a suitable material: TITLE: PLASTICS IN MEDICAL DEVICES: PROPERTIES, REQUIREMENTS, AND APPLICATIONS; 2ND EDITION; authored by Vinny R. SASTRI; hardcover ISBN: 9781455732012; published: 21 Nov. 2013; publisher: Amsterdam [Pays-Bas]: Elsevier/William Andrew.

Referring to the embodiment as depicted in FIG. 1, the elongated medical assembly 102 includes (preferably and is not limited thereto) a medical sheath assembly 103. The medical sheath assembly 103 is also called an elongated sheath, etc., and any equivalent thereof.

Figure 2:
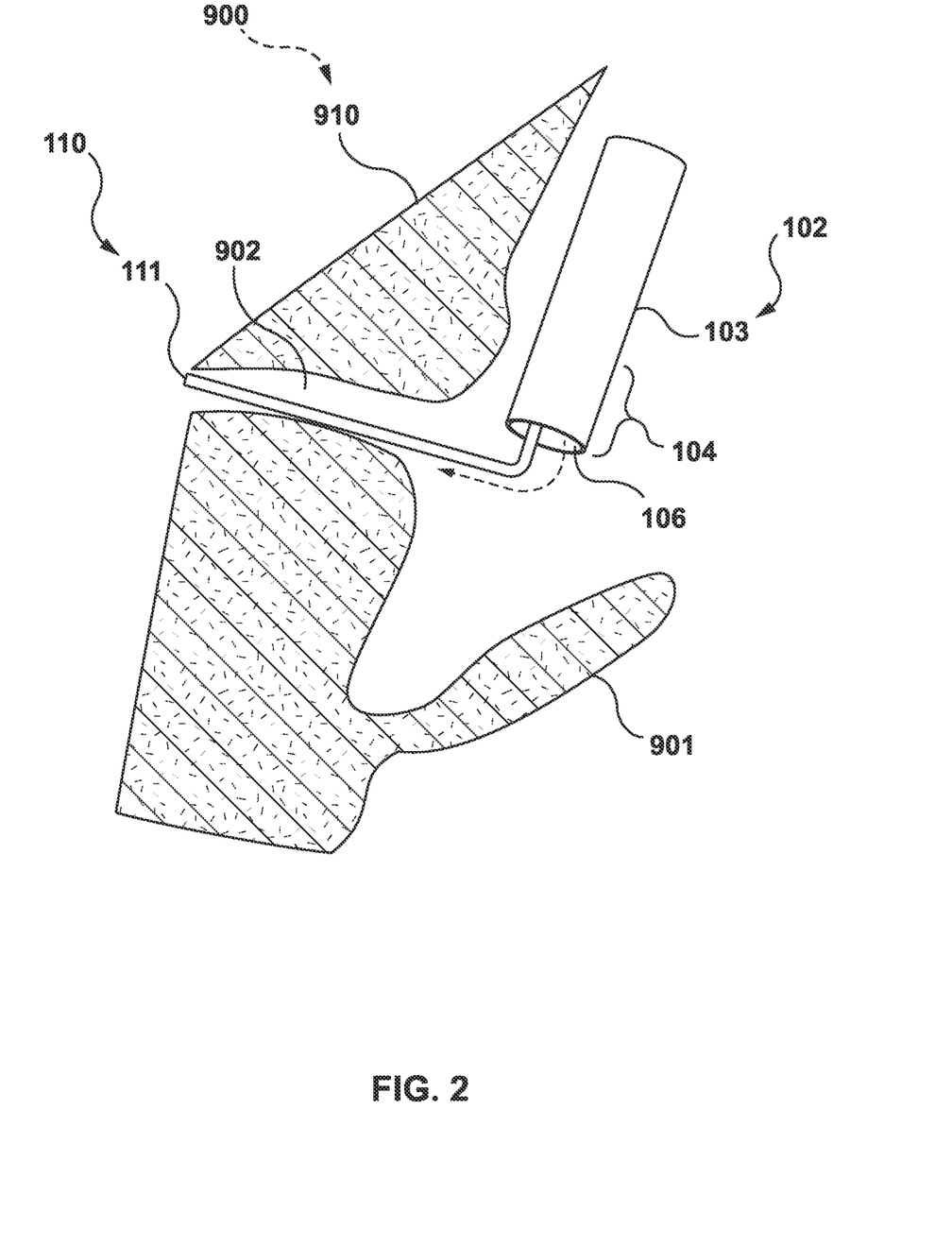
Figure 3:
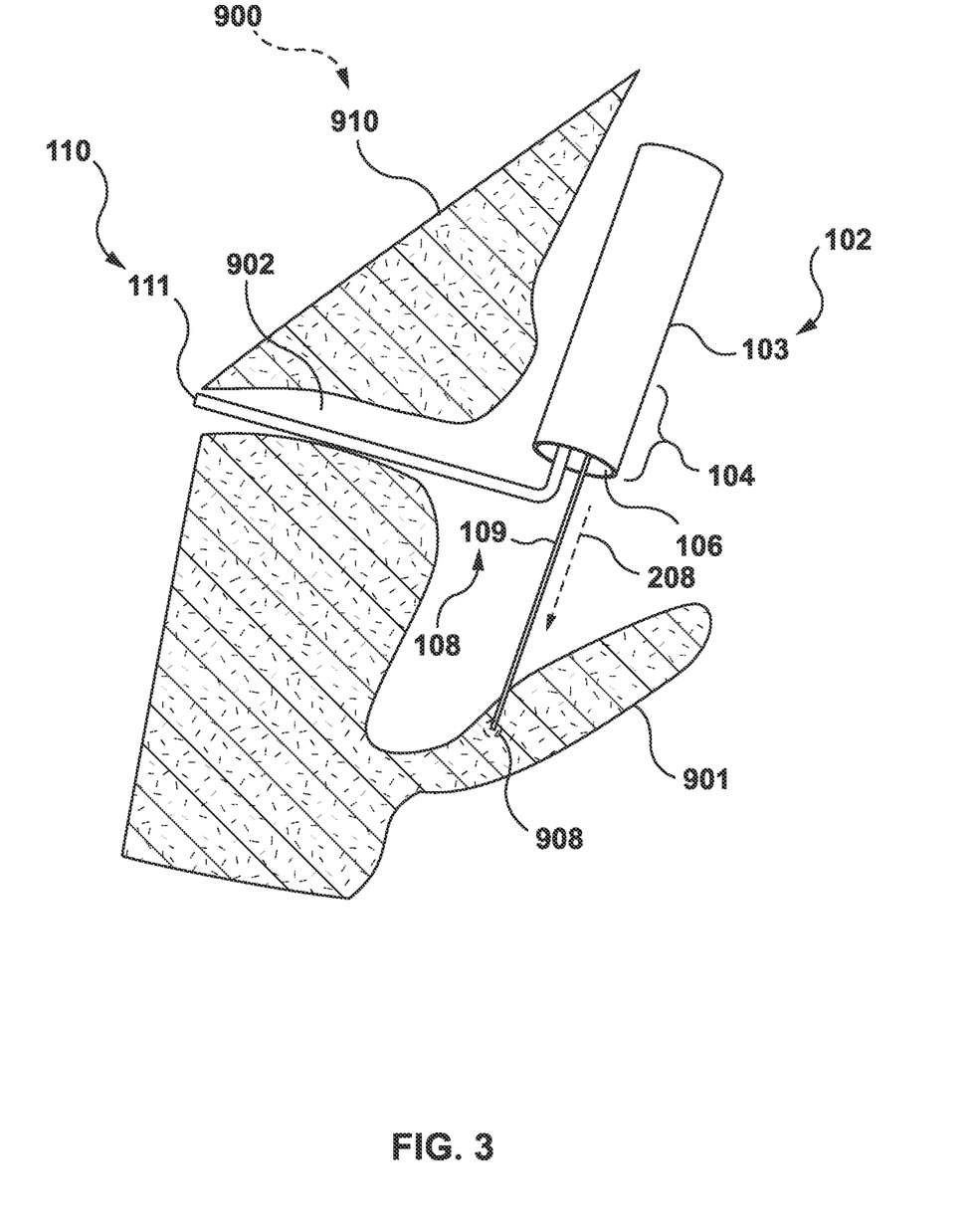
Figure 4:
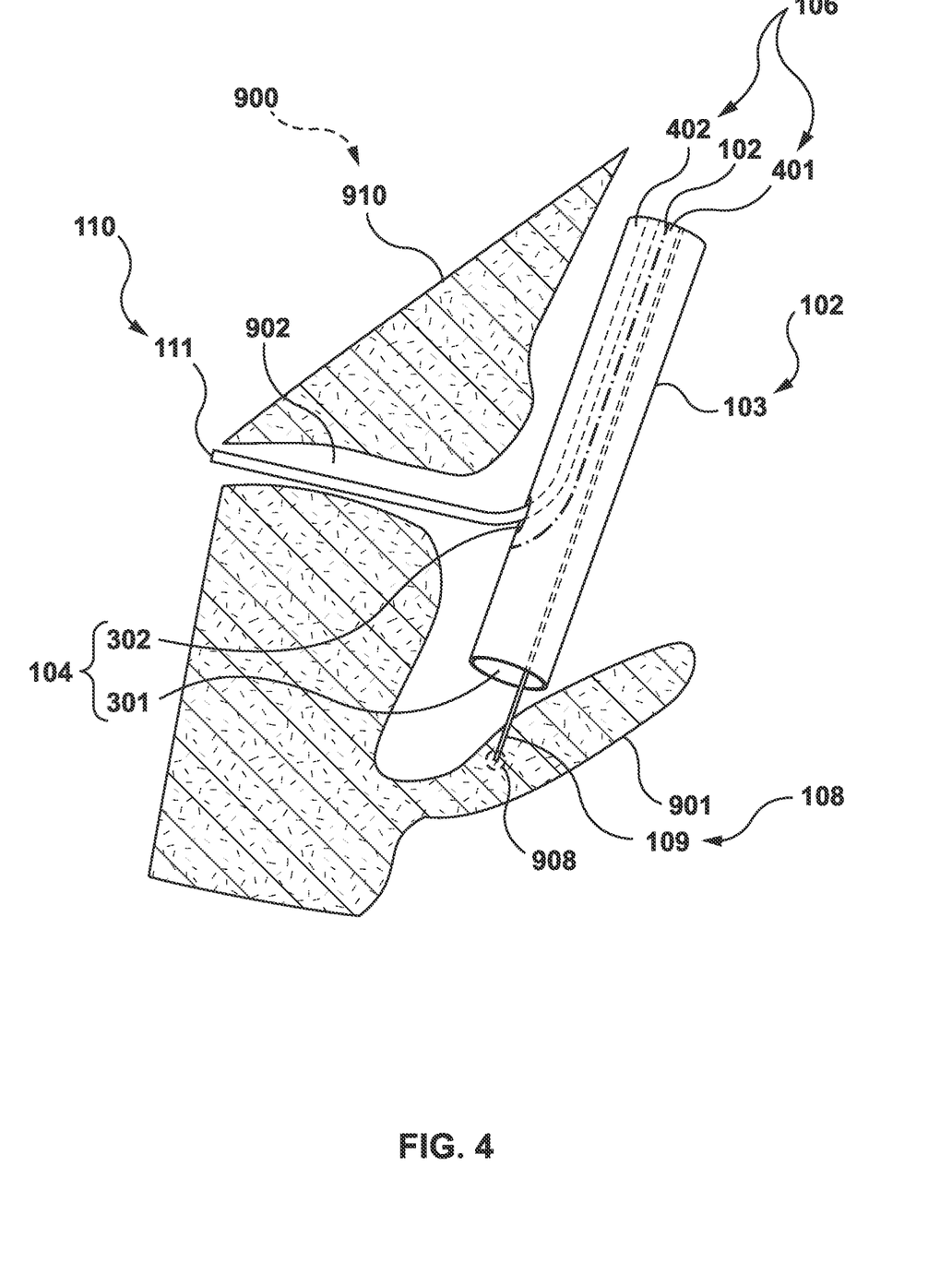

Referring to the embodiments as depicted in FIG. 2 and FIG. 3, the elongated medical assembly 102 is configured to facilitate movement (along the elongated length of the elongated medical assembly 102) of at least one, or more, medical devices. The medical sheath assembly 103 defines (provides) a lumen assembly 106 that extends, at least in part, along an elongated length of the medical sheath assembly 103. In accordance with a preferred embodiment, the lumen assembly 106 includes at least one lumen or at least one or more lumens (reference is made to the embodiment as depicted in FIG. 4, in which two lumens are depicted). The lumen assembly 106 is configured to receive, at least in part (along the elongated length of the medical sheath assembly 103) at least one or more medical devices The lumen assembly 106 is also configured to facilitate movement of at least one or more medical devices, such as a first medical device 110 (as depicted in FIG. 2 and FIG. 3) and/or a second medical device 108 (as depicted in FIG. 3), etc. The first medical device 110 may be advanced and retracted from the elongated medical assembly 102 (such as a medical sheath). The first medical device 110 is configured to form (at least in part) a bend (preferably, a perpendicular bend) when or once advanced (advanced fully or partially) from the lumen assembly 106 (that is, from a distal port assembly 104, or distal end, of the elongated medical assembly 102 leading out from the lumen assembly 106). In accordance with a preferred embodiment, the distal port assembly 104 includes at least one distal port or at least one or more distal ports (reference is made to the embodiment as depicted in FIG. 4, in which two distal ports are depicted). The second medical device 108 may share the elongated medical assembly 102, and the second medical device 108 may also be advanced and retracted by the operator, etc. For instance, the first medical device 110 includes an anchor device 111 (and any equivalent thereof). The first medical device 110 is configured to be movable (extendable or maneuverable by a user such as a surgeon performing a procedure) from the elongated medical assembly 102 along a first movement direction 210, as depicted in FIG. 2. The first movement direction 210 extends away from the elongated medical assembly 102 once the elongated medical assembly 102 is positioned proximate to the biological structure 910 of the patient 900. The first movement direction 210 may be any shape or alignment (curved, straight, etc.). For instance, the second medical device 108 includes a puncture device 109 (and any equivalent thereof). The puncture device 109 is configured to form, in any manner, a puncture hole 908 through a portion of the tissue of the patient 900. The second medical device 108 is configured to be movable (extendable or maneuverable by a user, such as a surgeon performing a procedure) from the elongated medical assembly 102 and along a second movement direction 208 (extending away the elongated medical assembly 102), once or after the elongated medical assembly 102 is positioned proximate to the biological structure 910 of the patient 900. The second movement direction 208 (as depicted in FIG. 3) may be any shape or alignment (curved, straight, etc.).

Referring to the embodiments as depicted in FIG. 2 and FIG. 3, the elongated medical assembly 102 is configured to be maneuverable proximate to a first biological feature 901 of a patient 900. The elongated medical assembly 102 has an elongated length. The elongated medical assembly 102 is also configured to facilitate movement of a first medical device 110 and a second medical device 108 along the elongated length of the elongated medical assembly 102.

Referring to the embodiments as depicted in FIG. 2 and FIG. 3, the first medical device 110 includes a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus applied to the shape-memory material. This is known as the shape memory effect (SME). Superelasticity (in alloys) may be observed once the shape-memory material is deformed under the presence (an application) of a stimulus force. The first medical device 110 includes (in accordance with an embodiment) superelastic nitinol. Nitinol alloys exhibit two closely related and unique properties: shape memory effect (SME) and superelasticity (SE; also called pseudoelasticity or PE). Shape memory is the ability of nitinol to undergo deformation at one temperature, and to then recover its original, undeformed shape upon being heated above its transformation temperature. Superelasticity occurs at a narrow temperature range just above its transformation temperature; in this case, no heating is necessary to cause the undeformed shape to recover, and the material exhibits enormous elasticity, from about ten (10) to thirty (30) times that of ordinary metal.

Referring to the embodiment as depicted in FIG. 3, the second medical device 108 includes, preferably, biocompatible materials.

Referring to the embodiment as depicted in FIG. 1, the elongated medical assembly 102 is configured to be inserted, at least in part, into an interior section of the patient 900 (and maneuverable along the interior of the patient 900). Once inserted, at least in part, into the patient 900, the elongated medical assembly 102 is configured to be maneuvered (movable) toward a position (a desired position or a target position) located proximate to the biological structure 910 (such as, the heart, etc.) of the patient 900. More specifically, the elongated medical assembly 102 is configured to be maneuvered proximate to a first biological feature 901 (such as, the valve leaflet of the heart, etc.) of the biological structure 910.

Referring to the embodiment as depicted in FIG. 2, the first medical device 110 (such as the anchor device 111) is configured to be supported (at least in part) by the elongated medical assembly 102 for maneuvered movement along (at least in part) the elongated medical assembly 102 (such as, along an elongated length of the elongated medical assembly 102). The anchor device 111 is configured to be maneuvered toward (an anchoring position located proximate to or into) a second biological feature 902 of the biological structure 910 (that is, this is done after the elongated medical assembly 102 is maneuvered proximate to the biological structure 910). For instance, the second biological feature 902 includes the right coronary artery (RCA) of the heart of the patient 900 (as depicted in FIG. 2), etc. For instance, the first biological feature 901 includes the valve leaflet of the heart of the patient 900 (as depicted). The second biological feature 902 of the patient 900 is spaced apart from the first biological feature 901. The anchor device 111 is configured to extend from (at least in part) the elongated medical assembly 102 (that is, from the distal port assembly 104 thereof) to (toward) the second biological feature 902 of the patient 900 (this is done in such a way that the anchor device 111 becomes securely positioned to the second biological feature 902). Preferably, this is done in such a way that the anchor device 111 becomes (may become) securely selectively positioned (anchored, wedged, friction fitted) to the second biological feature 902 by further movement of the anchor device 111. In this manner, the anchor device 111 is selectively locked to (selectively anchored to) a stationary position or an anchored condition (and is secured, for the time being, against further movement once securely positioned to (relative to) the second biological feature 902). Specifically, in this manner, the distal port assembly 104 of the elongated medical assembly 102 may become securely positioned to (relative to) the second biological feature 902; in this manner, the distal port assembly 104 may be positioned in a relatively stationary condition so that the distal port assembly 104 may become spatially oriented, or pointed to face toward (at least in part) the first biological feature 901. A subsequent deployment of the second medical device 108 may commence from the elongated medical assembly 102 (once the anchor device 111 is securely deployed, as depicted in FIG. 2). The anchor device 111 is configured to selectively anchor (securely selectively connect) the elongated medical assembly 102 to the second biological feature 902. It will be appreciated that once the anchor device 111 is no longer needed, the anchor device 111 is configured to selectively de-anchor (securely selectively disconnect or unconnect) the elongated medical assembly 102 from the second biological feature 902 (that is, in response to maneuvered motions (forces) imparted to the anchor device 111 by the user or the surgeon); this is done, preferably, by retracting (manually maneuvering) the anchor device 111 back toward the elongated medical assembly 102 (preferably, retracted back into the interior of the elongated medical assembly 102). It will be appreciated that the user or the surgeon has manual access to a proximal portion of the anchor device 111 that extends outwardly (known to those skilled in the art and not depicted) from the body of the patient 900. It will be appreciated that the user or the surgeon has manual access to a proximal portion of the puncture device 109 that extends outwardly (known to those skilled in the art and not depicted) from the body of the patient 900.

Referring to the embodiment as depicted in FIG. 3, the anchor device 111, in use, facilitates, in use, spatial oriented maneuvered movement of the second medical device 108 (such as the puncture device 109) from the elongated medical assembly 102 toward the first biological feature 901; this is done once, or after, the anchor device 111 extends toward and becomes securely selectively anchored to the second biological feature 902. The puncture device 109 is configured to be supported, at least in part, (by the elongated medical assembly 102) for maneuvered movement along (an elongated length of) the elongated medical assembly 102. The puncture device 109 is maneuvered (manually by the user) toward the first biological feature 901 (that is, once, or after, the anchor device 111 is maneuvered to, and secured into position with, the second biological feature 902). The puncture device 109 is configured to be utilized (such as, activated) for the formation of the puncture hole 908 (through the tissue of the patient 900); this is done in such a way that the puncture device 109, in use, forms the puncture hole 908 that extends through the first biological feature 901 (that is, once, or after, the puncture device 109 is maneuvered toward, and is positioned proximate to, the first biological feature 901 of the patient 900 for this purpose).

Referring to the embodiment as depicted in FIG. 3, the puncture device 109 includes (and is not limited to) a radio frequency puncture device, such as the BAYLIS (TRADEMARK) POWERWIRE (REGISTERED TRADEMARK) radio frequency guidewire manufactured by BAYLIS MEDICAL COMPANY (headquartered in Canada). In accordance with another embodiment, the puncture device 109 includes (and is not limited to) an elongated guidewire having a distal tip section presenting a mechanical cutting portion; for this case, the puncture hole 908 is formed by physically moving the mechanical cutting portion into the first biological feature 901.

Referring to the embodiment as depicted in FIG. 3, there is depicted an apparatus including (and is not limited to) a synergistic combination of the elongated medical assembly 102, the puncture device 109 and the anchor device 111. The elongated medical assembly 102 is configured to be maneuverable proximate to the first biological feature 901 of the patient 900. The puncture device 109 is configured to be, at least in part, supported for maneuvered movement along the elongated medical assembly 102. The anchor device 111 is configured to be, at least in part, supported for maneuvered movement along the elongated medical assembly 102. For instance, the anchor device 111 is configured to provide a reference position for facilitating the location, or the targeting of, a medical procedure (such as the correct location or position for a leaflet procedure, etc.). For instance, the anchor device 111 is configured to extend from the elongated medical assembly 102 to, and to be securely positioned to, the second biological feature 902 of the patient 900. The anchor device 111 is configured to extend from the elongated medical assembly 102 toward a second biological feature 902 of the patient 900 in such a way that the anchor device 111 becomes securely positioned to the second biological feature 902. Preferably, this is done in such a way that the anchor device 111 becomes securely selectively positioned to the second biological feature 902 (with further movement of the anchor device 111); the anchor device 111 is configured to facilitate (after the anchor device 111 is selectively secured) spatial oriented maneuvered movement of the puncture device 109 from the elongated medical assembly 102 to the first biological feature 901. This arrangement provides improved confidence (for the surgeon) for execution of the procedure.

Referring to the embodiment as depicted in FIG. 3, there is depicted an apparatus including (and is not limited to) a synergistic combination of the elongated medical assembly 102, the puncture device 109 and the anchor device 111. The elongated medical assembly 102 is configured to be maneuverable proximate to the first biological feature 901 of a patient 900. The elongated medical assembly 102 has a distal port assembly 104 leading to a lumen assembly 106 defined along, at least in part, an elongated length of the elongated medical assembly 102. The puncture device 109 is configured to be, at least in part, receivable into (extendable from and retractable into) the distal port assembly 104 of the elongated medical assembly 102. The puncture device 109 is also configured to be, at least in part, extendable, at least in part, along the lumen assembly 106 of the elongated medical assembly 102 (once or after the puncture device 109, in use, is received, at least in part, into the distal port assembly 104 of the elongated medical assembly 102). The anchor device 111 is configured to be, at least in part, receivable into (extendable from and retractable into) the distal port assembly 104 of the elongated medical assembly 102. The anchor device 111 is also configured to be extendable, at least in part, along the lumen assembly 106 of the elongated medical assembly 102 (that is, once, or after, the puncture device 109, in use, is received, at least in part, into the anchor device 111 of the elongated medical assembly 102). Preferably, the anchor device 111 is configured to provide a reference position for facilitating the location (for the targeting of) a medical procedure. Preferably, the anchor device 111 is configured to be maneuvered and extended, at least in part, from the elongated medical assembly 102 toward (and to be securely positioned to) the second biological feature 902 of the patient 900; this is done in such a way that the anchor device 111 (A) becomes securely positioned to the second biological feature 902, and (B) facilitates, in use, spatial oriented maneuvered movement of the puncture device 109 from the elongated medical assembly 102 toward the first biological feature 901.

Referring to the embodiment as depicted in FIG. 3, the first biological feature 901 includes the valve leaflet, and the second biological feature 902 includes the right coronary artery (RCA). The anchor device 111 is configured to be maneuvered, at least in part, into an opening of the right coronary artery (RCA), and anchored thereto. The puncture device 109 is configured to be maneuvered, at least in part, toward the first biological feature 901, in which the first biological feature 901 includes the valve leaflet (that is, after, or once, the anchor device 111 is maneuvered, at least in part, into the opening of the right coronary artery (RCA), and anchored thereto).

Referring to the embodiments as depicted in FIG. 1, FIG. 2, FIG. 3 and FIG. 4, there is provided (depicted) a method of operating an elongated medical assembly 102. The method includes and is not limited to maneuvering, at least in part, the elongated medical assembly 102 to a position located proximate to the first biological feature 901 of the patient 900. The method also includes maneuvering, at least in part, the puncture device 109 (wire) along the elongated medical assembly 102. The method also includes maneuvering, at least in part, the anchor device 111 along the elongated medical assembly 102. The method may also include maneuvering, at least in part, the anchor device 111 to provide a reference for facilitating the targeting of a procedural location (such as, location of the correct valve leaflet and/or an optimal leaflet location, etc.). The method may also include maneuvering, at least in part, the anchor device 111 from the elongated medical assembly 102 toward the second biological feature 902, and securely positioning the anchor device 111 to the second biological feature 902 of the patient 900; this is done in such a way that the anchor device 111 becomes securely positioned to the second biological feature 902, and the anchor device 111 facilitates, in use, spatial oriented maneuvered movement of the puncture device 109 from the elongated medical assembly 102 toward the first biological feature 901.

Referring to the embodiments as depicted in FIG. 1, FIG. 2, FIG. 3 and FIG. 4 the method may also include having the first biological feature 901 include the valve leaflet, and the second biological feature 902 include the right coronary artery (RCA). The method may further include maneuvering, at least in part, the anchor device 111 into an opening of the right coronary artery (RCA). The method may further include maneuvering, at least in part, the puncture device 109 toward the valve leaflet once, of after, the anchor device 111 is maneuvered, at least in part, into the opening of the right coronary artery (RCA), and anchored thereto.

Referring to the embodiment as depicted in FIG. 4, the distal port assembly 104 (of the elongated medical assembly 102) includes at least one distal port or at least one or more distal ports, such as a first distal port 301 and a second distal port 302. The second distal port 302 spaced apart from the first distal port 301. In accordance with a preferred embodiment, the first distal port 301 is positioned at a distal tip portion (distal end) of the elongated medical assembly 102. In accordance with a preferred embodiment, the second distal port 302 is positioned (located) on the circumferential side wall of the elongated medical assembly 102.

Referring to the embodiment as depicted in FIG. 4, the lumen assembly 106 (of the elongated medical assembly 102) includes at least one lumen or at least one or more lumens, such as a first lumen 401 and a second lumen 402. Preferably, the elongated medical assembly 102 defines the first lumen 401 and the second lumen 402. Preferably, an interior elongated wall 112 separates the first lumen 401 and the second lumen 402. The first lumen 401 extends from the first distal port 301. The second lumen 402 extends from the second distal port 302. The first lumen 401 and the second lumen 402 extend, at least in part, along an elongated length of the elongated medical assembly 102 (and along the interior of the elongated medical assembly 102).

Referring to the embodiment as depicted in FIG. 4, the first distal port 301 and the first lumen 401 are configured to receive (to facilitate movement of) the second medical device 108 (or the puncture device 109). The second distal port 302 and the second lumen 402 are configured to receive (to facilitate movement of) the first medical device 110 (or the anchor device 111).

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. A method of operating an elongated medical assembly, the method comprising:
   maneuvering, at least in part, the elongated medical assembly to a position located proximate to a valve leaflet of a heart of a patient;
   maneuvering, at least in part, a puncture device along the elongated medical assembly;
   maneuvering, at least in part, an anchor device along the elongated medical assembly into an opening of the right coronary artery and securely positioning the anchor device to the opening in such a way that the anchor device facilitates spatially oriented maneuvered movement of the puncture device from the elongated medical assembly toward the valve leaflet; and
   maneuvering, at least in part, the puncture device toward the valve leaflet once the anchor device is anchored to the opening.

2. A system for performing a procedure on a valve leaflet of a patient's heart, the system comprising:
   a delivery sheath having a longitudinal lumen and a distal end port and a distal side port disposed proximal to the distal end port, the elongated medical device configured to be maneuverable to the patient's heart such that the distal end port is proximate a the valve leaflet and the distal side port is proximate an opening to the right coronary artery;
   an anchor device configured to be advanced through the lumen of the delivery sheath and to exit the delivery sheath through the distal side port; and a puncture device configured to form a puncture hole through the valve leaflet, the puncture device configured to be advanced through the lumen of the delivery sheath and to exit the distal end port;

wherein, the anchor device is configured to enter the opening of the right coronary artery and anchors therein, upon exiting the distal side port, so as to provide a reference position for the delivery sheath; and further wherein, upon anchoring of the anchor device to the opening of the right coronary artery, the puncture device is configured to advance to a location proximate the heart valve leaflet.

3. The system of claim 2 wherein the lumen includes a first lumen extending through the delivery sheath to the distal side port and a second lumen extending through the delivery sheath to the distal end port.

* * * * *